United States Patent [19]

Krespan

[11] 4,005,104

[45] Jan. 25, 1977

[54] PRODUCTS FROM THE REACTION OF SULFUR TRIOXIDE WITH ACYCLIC INTERNAL VIC-DIALKOXYPOLYFLUOROALKENES

[75] Inventor: Carl George Krespan, Wilmington, Del.

[73] Assignee: E. I. Du Pont de Nemours and Company, Wilmington, Del.

[22] Filed: Aug. 15, 1975

[21] Appl. No.: 604,932

[52] U.S. Cl. .................... 260/327 H; 260/593 H; 252/8.7
[51] Int. Cl.² .................................... C07D 327/10
[58] Field of Search ............. 260/327 H, 593 H

[56] References Cited

UNITED STATES PATENTS 3,055,913  9/1962  Moore et al. .................. 260/327

Primary Examiner—Natalie Trousof
Assistant Examiner—C. M. S. Jaisle

[57] ABSTRACT

Selected novel vic-dialkoxyperfluoroalkyl-vic-diol cyclic sulfates, e.g., 2,3-dimethoxyhexafluorobutane-2,3-diol cyclic sulfate, useful for preparing the corresponding perfluoro-α-diketones, e.g., hexafluorobiacetyl (known), are synthesized by reacting $SO_3$ with a vic-dialkoxypolyfluoroalkene, e.g., 2,3-dimethoxyhexafluorobutene-2.

8 Claims, No Drawings

PRODUCTS FROM THE REACTION OF SULFUR TRIOXIDE WITH ACYCLIC INTERNAL VIC-DIALKOXYPOLYFLUOROALKENES

BACKGROUND OF THE INVENTION

1. Field of the Invention

This invention relates to vic-dialkoxyperfluoroalkyl-vic-diol cyclic sulfates and corresponding perfluoro-$\alpha$-diketones.

2. Prior Art

The oxidation of 2,3-dichloro-1,1,1,4,4,4-hexafluoro-2-butene with fuming sulfuric acid to yield perfluorobiacetyl and 2,3-dichloro-1,1,1,4,4,4-hexafluoro-2,3-butanediol cyclic sulfate is disclosed in Moore and Clark U.S. Pat. No. 3,055,913.

L. O. Moore in J. Org. Chem., 35 3999 (1970) discloses the conversion of 2,3-dichloro-1,1,4,4-hexafluoro-2,3-butanediol cyclic sulfate

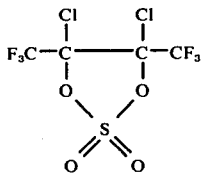

to perfluorobiacetyl

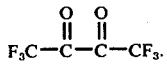

SUMMARY AND DETAILED DESCRIPTION OF THE INVENTION

The present invention discloses a process (A) for the preparation of

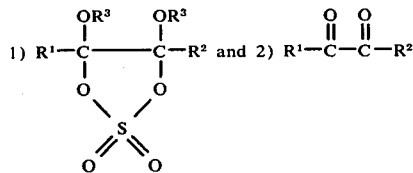

wherein $R^1$ and $R^2$ can be alike or different and are perfluoroalkyl of up to 6 carbon atoms and $R^3$ is methyl or ethyl, said process comprising reacting $R^1C(OR^3) = C(OR^3)R^2$ in the presence of $SO_3$ at a temperature of $-40°$ to $100°$ C and (B) the conversion of (1) to (2) by further treatment with concentrated sulfuric acid.

The internal vic-dialkoxyperfluoroalkyl-vic-diol cyclic sulfate and the perfluoro-$\alpha$-diketone reaction products of the present invention are prepared by first preparing internal vic-dialkoxyfluoroalkene by means of reacting internal perfluoroalkene with a sodium alkoxide. The internal vic-dialkoxyfluoroalkene is then reacted with $SO_3$ at temperatures of $-40° - 100°$ C, preferably $0°-40°$ C, to form the cyclic sulfate and perfluoro-$\alpha$-diketone. The cyclic sulfate may then be converted to the perfluoro-$\alpha$-diketone in high yields by reaction with concentrated sulfuric acid. Alternatively, if the perfluoro-$\alpha$-diketone is the sole product desired the internal vic-dialkoxypolyfluoroalkene may be reacted with fuming sulfuric acid.

In a preferred embodiment, $CF_3(OCH_3) = C(OCH_3)CF_3$ is reacted with $SO_3$ to form 1) 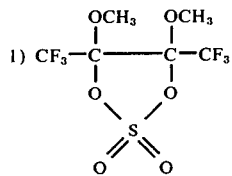

and

2) 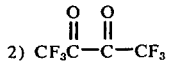

at a temperature of $0°-40°$ C.

In the preferred mode of the process, perfluorobutene-2 is reacted with sodium methoxide to form 2,3-dimethoxyhexafluorobutene-2 (I). This intermediate is then treated with $SO_3$ at temperatures of $0°-40°$ C to form 2,3-dimethoxyhexafluorobutane-2,3-diol cyclic sulfate (II) and hexafluorobiacetyl (III). An excess of either reactant may be used if desired, but preferred is an $SO_3$: olefin reactant mole ratio close to 2:1. Pressure is not important, but may vary from much less than one atmosphere to 1000 psi. A solvent is not necessary, but a solvent of low reactivity to sulfur trioxide may be used, especially halogenated solvents such as tetrachloroethylene and 1,1,2-trichloro-1,2,2-trifluoroethane. Reaction time can vary from less than a minute to several hours depending on conditions, but will generally be less than 15 min. Isolation is effected by distillation under reduced pressure. The more volatile hexafluorobiacetyl is removed first and then the higher boiling cyclic sulfate removed. The distilled cyclic sulfate in crude form may be then reacted with concentrated sulfuric acid to form hexafluorobiacetyl in good yields.

SPECIFIC EMBODIMENTS OF THE INVENTION

The following example will serve to illustrate the practice of the invention. In this example, as throughout the application, temperatures are in degrees centigrade and percentages are by weight.

EXAMPLE 2,3-Dimethoxyhexafluorobutane-2,3-diol Cyclic Sulfate and Hexafluorobiacetyl

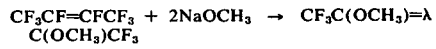

A mixture of 112.5 g (0.56 mol) of perfluorobutene-2 and 200 ml of methanol was stirred at $0°-5°$ while a solution of 64.8 g (1.2 mol) of sodium methoxide in 350 ml of methanol was added over a one-hour period. The mixture was allowed to come to 25°, stirred overnight, and refluxed for 2 hr. Most of the methanol was distilled off and the distillate shaken with 1.2 l. of $H_2O$. The lower layer was separated, combined with the higher boiling residue and the whole washed three times with 1.2 l. of $H_2O$. The product layer was then dried over $CaCl_2$, filtered and distilled to give a mixture of cis-trans isomers of I, bp $68°-74°$ (250 mm), 63.6 g (51%). Ir(CCl₄) 3.31, 3.37, and 3.49 (satd CH), 6.04 (C=C), 7.5–9μ (CF, COC): nmr ¹H 3.83 (s, cis OCH₃), 3.73 ppm (s, trans OCH₃); ¹⁹F −65.4 (s, cis CF₃), −65.7 ppm (trans CF₃).

Anal. Calcd for $C_6H_6F_6O_2$: C, 32.16; H, 2.70; F, 50.87; Found: C, 32.40; H, 3.06; F, 50.82

The use of glyme (59%) or tetrahydrofuran (66%) as reaction medium at low temperature gave improved yields, even for a reaction carried out at −40° with inverse addition, but thorough water washing is essential to remove solvent. Otherwise the ether solvent tends to codistil with product, bp 94°–100° when pure.

The analysis and an extraneous $CH_3O$ band in the ¹H nmr spectrum indicate the presence of a small amount of dimethyl sulfate as an impurity. The identity of II was confirmed by converting it to III in high yield with sulfuric acid.

Part C

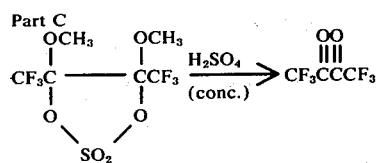

Part B

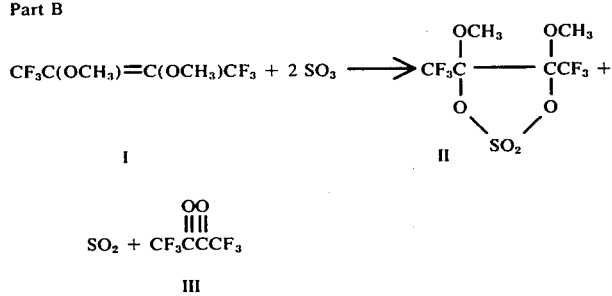

A mildly exothermic reaction of 44.8 g (0.20 mol) of I and 36.0 g (0.45 mol) of SO₃ was kept below 45° by external cooling during the SO₃ addition. The mixture was then heated at 100°–110° at one atm while volatiles were collected in a cold trap. Distillation of the volatiles gave considerable SO₂ (identified by ir) and 9.3 g (24%) of yellow hexafluorobiacetyl III, bp 19°–20° (lit. bp 20°).

Distillation of higher boilers gave 43.2 g (68%) of cis-trans isomers of II, bp 77°–89° (40 mm). IR (CaF₂ plates) 3.30, 3.35, and 3.47 (satd CH), 6.98 (SO₂O), 7.6–8.7μ (CF, SO₂): nmr ¹H 3.89 (s, OCH₃), 3.78 ppm (m, OCH₃); ¹⁹F-74.5 (m, CF₃), −76.9 ppm (s, CF₃).

Anal. Calcd for $C_6H_6F_6O_6S$: C, 22.51; H, 1.89; F, 35.60; S, 10.01. Found: C, 22.41; H, 2.14; F, 33.30; S, 10.96.

A mixture of 38.8 g (0.12 mol) of crude II and 100 ml of conc. H₂SO₄ (2 layers) was stirred and heated to 80°, where formation of III commenced. The mixture was slowly heated to 120° while III was collected in a cold trap, 18.4 g (79%), identified as pure III by ir.

Substitution of sodium ethoxide for the methoxide in Part A. would yield the corresponding ethyl ether which would react identically as the methyl ether in Part B.

The Table which follows shows that, when the procedures of the example are followed and the initial fluoroolefin is reacted with sodium methoxide (or ethoxide) and the product further reacted with SO₃, the cyclic sulfate and perfluoro-α-diketones are obtained.

TABLE

| Perfluoroolefin | vic-alkene | Cyclic Sulfate | Diketone |
|---|---|---|---|
| $CF_3CF=CFCF_2CF_3$ | (1) $CF_3C(OCH_3)=C(OCH_3)CF_2CF_3$ | $CF_3C(OCH_3)(O)—C(OCH_3)(O)CF_2CF_3$ with SO₂ bridge | $CF_3C(O)C(O)CF_2CF_3$ |
| $CF_3CF_2CF=CFCF_2CF_3$ | (2) $CF_3CF_2C(OCH_3)=C(OCH_3)CF_2CF_3$ | $CF_3CF_2C(OCH_3)(O)—C(OCH_3)(O)CF_2CF_3$ with SO₂ bridge | $CF_3CF_2C(O)C(O)CF_2CF_3$ |
| $CF_3(CF_2)_3CF=CFCF_3$ | (3) $CF_3(CF_2)_3C(OCH_3)=C(OCH_3)CF_3$ | $CF_3(CF_2)_3C(OCH_3)(O)—C(OCH_3)(O)CF_3$ with SO₂ bridge | $CF_3(CF_2)_3C(O)C(O)CF_3$ |

TABLE-continued

| Perfluoroolefin | vic-alkene | Cyclic Sulfate | Diketone |
| --- | --- | --- | --- |
| $CF_3CF=CFCF(CF_3)_2$ | (4) $CF_3\underset{\underset{OCH_3}{\mid}}{C}=\underset{\underset{OCH_3}{\mid}}{C}CF(CF_3)_2$ | $CF_3\underset{\underset{O}{\mid}}{\overset{\overset{OCH_3}{\mid}}{C}}\underset{SO_2}{\diagdown\diagup}\underset{\underset{O}{\mid}}{\overset{\overset{OCH_3}{\mid}}{C}}CF(CF_3)_2$ | $CF_3\overset{O}{\overset{\|}{C}}\overset{O}{\overset{\|}{C}}CF(CF_3)_2$ |

Notes:
(1) The starting perfluoroolefin is found in "Advances in Fluorine Chemistry," Vol. 3, Stacey, Tatlow, and Sharpe, Eds., Butterworths, Washington, D. C., 1963, p 226.
(2) The starting perfluoroolefin is found in Lovelace, Rausch, and Postelnek, "Aliphatic Fluorine Compounds," Reinhold Pub. Co., N.Y., N.Y., 1958, p 120.
(3) The starting perfluoroolefin is found in "Advances in Fluorine Chemistry," Vol. 4, Stacey, Tatlow, and Sharpe, Eds., Butterworths, 1965, p 72.
(4) The starting perfluoroolefin is found in "Advances in Fluorine Chemistry," Vol. 4, Stacey, Tatlow, and Sharpe, Eds., Butterworths, 1965, p 74.

Utility 2,3-Dimethoxyhexafluorobutane-2,3-diol cyclic sulfate is useful as an intermediate, being converted to perfluoroiacetyl by reaction with sulfuric acid in good yields. Perfluorobiacetyl is useful in treating textiles such as cotton to impart wash and wear characteristics thereto. Similarly, the other cyclic sulfates of the invention can be converted to the corresponding known diketones.

All the novel cyclic sulfates of the invention are also useful as cationic initiators, e.g., in vinyl polymerization.

Thus, 6.2 g of 2-methoxyethyl vinyl ether, $CH_3OCH_2CH_2OCH=CH_2$, and 0.2 g of 2,3-dimethoxyhexafluorobutane-2,3-diol cyclic sulfate were mixed at 20°. There may have been a slight warming on mixing, but the colorless mixture gave no noticeable change for 5–10 min. Then an exotherm sent the temperature to about 50°. A yellow color developed after a total of 20 min. The mixture was cooled to below 25° and let stand. Another exotherm was noted and the mixture was cooled again. This process was repeated through four coolings before the exotherm became minor (about 1 hr). The very thick mixture was allowed to stand at 25° for another 3 hr., then evacuated at 20.5 min. and 25° for one day. 6.0 g (97% yield) of residual viscous polymer was obtained.

Mol wt. (bp elevation in benzene) = 2700.
Degree of polymerization = 26.5.

This diol is thus an effective initiator. The polymer produced would be itself useful as a plasticizer for polymeric resins when pressed into film form A as an antistatic agent.

All the perfluoro-α-diketones of the invention are useful as photoinitiators in radical polymerization according to the Drysdale U.S. Pat. Nos. 3,012,069 and 3,240,811.

I claim:
1. A compound of the formula

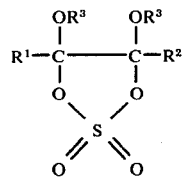

wherein: $R^1$ and $R^2$, alike or different, are perfluoroalkyl of up to 6 carbons, and $R^3$ is methyl or ethyl.

2. The compound of claim 1, 2,3-dimethoxyhexafluorobutane-2,3-diol cyclic sulfate.

3. The compound of claim 1 wherein $R^1$ and $R^2$ are each up to 4 carbons and total no more than 5 carbons.

4. The process of preparing a compound of claim 1 which comprises reacting, at a temperature of about −40 to 100° C, $SO_3$ with an alkene of the formula $R^1C(OR^3)=C(OR^3)R^2$ wherein $R^1$, $R^2$, and $R^3$ are as in claim 1.

5. The process of claim 4 wherein the alkene is $CF_3(OCH_3)C=C(OCH_3)CF_3$.

6. The process of claim 4 wherein $R^1$ and $R^2$ are each up to 4 carbons and total no more than 5 carbons.

7. The process of preparing an α-diketone which comprises reacting a compound of claim 1 with sulfuric acid.

8. The process of claim 7 which comprises reacting 2,3-dimethoxyhexafluorobutane-2,3-diol cyclic sulfate with sulfuric acid.

* * * * *